United States Patent [19]

Woelfel

[11] Patent Number: 5,035,616
[45] Date of Patent: Jul. 30, 1991

[54] DEVICE FOR SEPARATING THE PREMOLARS AND MOLARS

[75] Inventor: Julian B. Woelfel, Columbus, Ohio

[73] Assignee: Girrbach Dental GmbH, Pforzheim, Fed. Rep. of Germany

[21] Appl. No.: 443,460

[22] Filed: Nov. 30, 1989

[30] Foreign Application Priority Data

Nov. 30, 1988 [DE] Fed. Rep. of Germany .................. 3840350135

[51] Int. Cl.⁵ ............................................ A61C 19/04
[52] U.S. Cl. ................................................... 433/72
[58] Field of Search ...................... 433/148, 149, 72; 33/513, 514, 562

[56] References Cited

U.S. PATENT DOCUMENTS

| | | | |
|---|---|---|---|
| 2,891,313 | 7/1955 | Crowley | 433/149 |
| 3,510,948 | 10/1968 | Walthall | 433/149 |
| 3,763,565 | 10/1973 | Faust et al. | 433/72 |
| 4,571,181 | 2/1986 | Berger | 433/72 |
| 4,654,005 | 3/1987 | Woelfel | 433/72 |

OTHER PUBLICATIONS

Woelfel, J. F., D.D.S., "Craniomandibular Function and Dysfunction", *The Journal of Prosthetic Dentistry*, vol. 56, No. 6, Dec. 1986, pp. 716-727.

*Primary Examiner*—John J. Wilson
*Assistant Examiner*—Cindy A. Cherichetti
*Attorney, Agent, or Firm*—Spensley Horn Jubas & Lubitz

[57] ABSTRACT

A device for separating the molars and fixing the two jaw joints of a patient in centric relation the device being in the form of a curved shaped article having a front member which is to be introduced between the incisors via a front end of the member for eliminating contact between the molars and for support purposes, with the thickness of the front member decreasing toward the front end. Depending on the extent of penetration of the shaped article into the mouth of the patient between the upper and lower incisors, the thickness of the shaped article and hence the separation of the incisors can be read off from markings on the top of the shaped article. By varying this thickness over the front measurement portion of the shaped article, the dentist can ascertain and read off the smallest possible opening angle (incisor separation) at which the molars in a centric jaw position are separated, and this measurement value can be used as a reproducible variable for any further diagnostic or therapeutic manipulation. The shaped article is easy to manufacture, and easy to clean and sterilize, and permits an extremely precise and accurate, reproducible molar separation in centric relation.

21 Claims, 1 Drawing Sheet

U.S. Patent          July 30, 1991          5,035,616
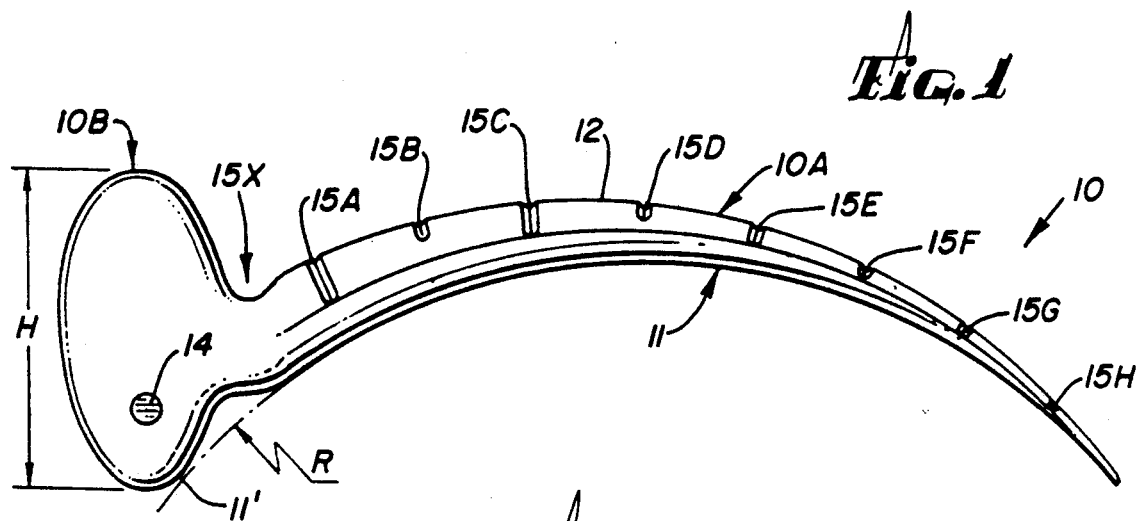
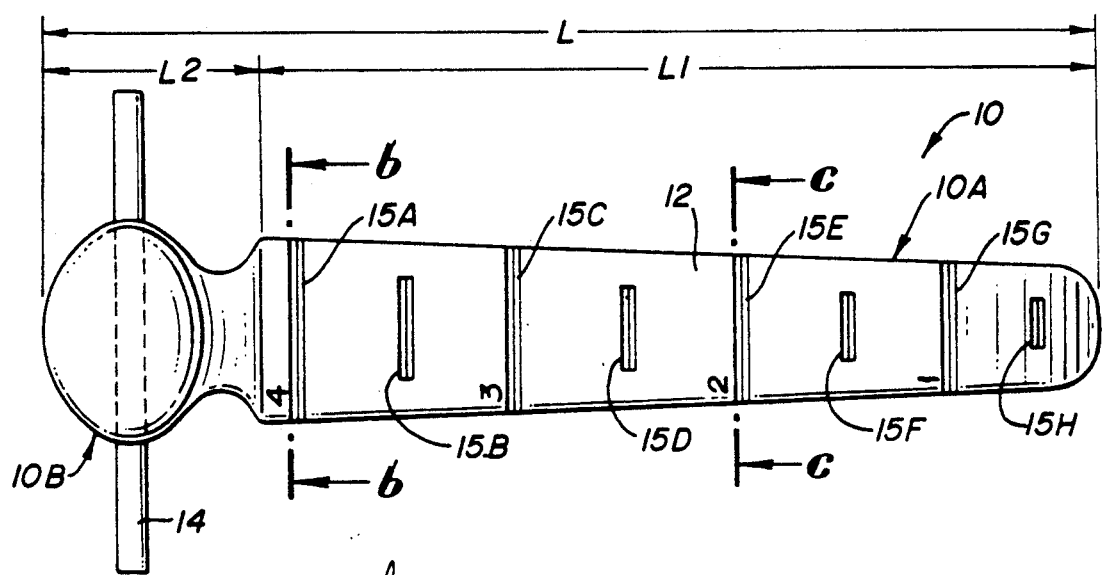
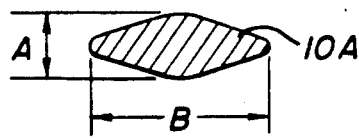
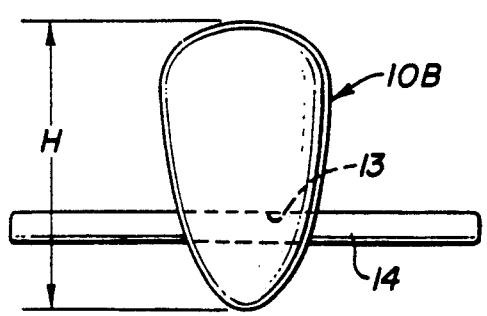
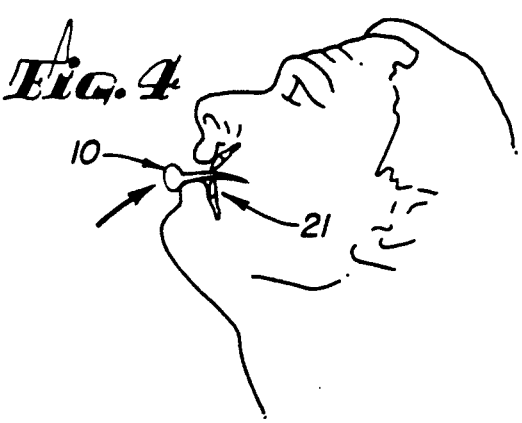

DEVICE FOR SEPARATING THE PREMOLARS AND MOLARS

BACKGROUND OF THE INVENTION

The invention relates to a device for preventing contact between the upper and lower premolars and molars of a patient in order to prevent the transfer of neural information, generated by tooth contact in the vicinity of the masticatory apparatus and at the same time to fix the mandible in a centric relation position of the temporomandibular joints at the smallest possible opening angle. The term "centric relation position" is understood to mean the most posterior position of the jaw hinges from which the mandible describes a purely rotational motion. On an articulator, this is the initial position for any peripheral movement. This joint position is an eminently important measurement variable in prosthetics, because it is reproducible and is the initial point of any mandibular motion. In transferring the maxillary and mandibular dental casts into an articulator, a row of teeth, for example the row of the maxilla, must be associated with respect to the patient to the axis of rotation of the articulator, and in a second phase the mandible must be associated with the already articulated-in maxilla in precisely this centric relation position. This provides largely coherent geometrical preconditions for motion simulation between the motion simulator and the patient.

The purpose of interrupting the neural impulses (deprogramming) is to recognize problematic influences (premature contacts, dysfunctions) in the diagnostic phase and to suppress them in the phase of odontoscopy in centric relation, during which the mandible cast is attached to the articulator.

By introducing a suitable device between the front teeth of the upper jaw, or maxilla, and lower jaw, or mandible, the tooth contacts can be infinitely graduatedly overcome, and with a suitable head posture, both jaw joints are compulsorily brought into a centric position (extreme dorsal/cranial posterior position) and kept in this position by supporting the front teeth on the device.

Leaf gauges have for instance been used until now as a suitable device for this purpose; for hygienic reasons and because of the danger of injury, instead of metal foils, thin plastic sheets have been combined in bundles in these gauges, but unlike the feeler gauges known in tool construction, the sheets are of uniform thicknesses. These leaf gauges are somewhat inconvenient to use; the required thickness for spacing apart of the front teeth must be continually corrected and adjusted by inserting small leaves or plates and removing them again, or adding or subtracting them. The magnitude of the distance, once found, is recorded by counting off the required number of leaves. This leaf gauge is difficult to sterilize.

In the article by Woelfel, entitled "Craniomandibular Function and Dysfunction", *The Journal of Prosthetic Dentistry*, Vol. 56, No. 6, December 1986, pp. 716 ff., a status description of some methods and apparatus for recording the jaw relation in the centric relation position is given. There is described a new centric relation system which includes a leaf gauge composed of a number of paper strips joined together along a short side, giving the gauge the shape of a long, narrow book or notepad. The individual "pages" of this book are of different colors and thus marked as blocks of variable thickness, so that certain standard thicknesses can be joined together. Since the front teeth on the one hand must now be spaced apart at least far enough to take the premolars and molars out of contact with one another, yet on the other hand the smallest possible opening angle must be sought (to prevent forward motion of the jaw joints), individual sheets must be removed or added, until both goals (teeth out of contact at minimum possible opening) are attained.

The removal and addition of individual sheets make this paper notepad relatively inconvenient to manipulate, and the accuracy which they achieve is questionable because of the resiliency, or compressibility of the paper or sliding of the layers of paper over one another. Ascertaining the actual thickness is more difficult, so repeatability for later procedures is not assured. Since the sheets can be used only once, it is also relatively expensive to use. This gauge is also described in U.S. Pat. No. 4,654,005.

SUMMARY OF THE INVENTION

It is therefore an object of the present invention to provide a simple device for the aforementioned purpose, which enables accurate, reliably repeatable recordings.

According to the invention, these and other objects are achieved by a device composed of a curved shaped article, particularly of a non-brittle, autoclavable plastic, having a thin front portion via which the device is introduced between the incisors and which increases in thickness in a continuously graduated manner.

A shaped article of this kind is simple to produce and extremely simple and precise in use: Since the thickness of the front portion, which is removed for the measurement, in an exemplary embodiment of the device increases from 0 to 4 mm over a length of approximately 50 mm, even slight changes in thickness of the device correspond to substantially greater and thus more easily recognized and read changes in the position of the incisors on the surface of the shaped article. According to a preferred embodiment of the invention, the result is a step-up ratio of approximately one to twelve, or in other words a change in the thickness of the shaped article of 1 mm corresponds to a longitudinal spacing between associated thickness markings on its surface of approximately 1.2 cm.

With this shaped article, measurements of the spacing between the upper and lower incisors can be performed extremely rapidly, simply and precisely and are replicable, because of the measuring scale. In addition, this article guides the lower jaw hinges into the centric relation position, which is the most neurologically sound and comfortable position.

According to one feature of the invention, the underside of the shaped article has the form of a circular arc, at least in its front section. This assures that the shaped article, when it is introduced between the upper and lower incisors, will not strike the palate inside the mouth.

According to a further feature of the invention, the cross section of the front portion of the shaped article used for the measurement is a rhomboid with rounded corners. The rhomboid shape enables an additional centering of the shaped article for measurement in the gap between the two upper and two lower incisors, which contributes substantially to defining a reproducible position and hence to attaining reproducible measurement results.

The invention also advantageously provides that the thickness of the front portion is specified on its top in the form of markings, so that the measurement result is easy to read off. If the markings are provided in the form of shallow grooves or notches, then this makes it possible to firmly hold the device in a predetermined position between the incisors, for example in order to quickly relax the jaw musculature.

Further features of the device according to the invention are defined by the other dependent claims.

An exemplary embodiment of the device according to the invention is described in further detail below with reference to the drawings.

BRIEF DESCRIPTION OF THE DRAWINGS

FIG. 1 is a side view of a preferred embodiment of a separation device according to the present invention.

FIG. 2a is a plan view of the device of FIG. 1.

FIGS. 2b and 2c are two cross-sectional views along line b—b and c—c of FIG. 2a.

FIG. 3 is a front elevational view of the device of FIGS. 1 and 2.

FIG. 4 is a pictorial elevational view showing the device according to the invention in use.

DESCRIPTION OF THE PREFERRED EMBODIMENTS

The device shown in FIGS. 1-4 is constituted by a shaped article, or gauge, 10 having a front portion 10A with a longitudinal dimension L1. Front portion 10A is used for the measurement procedure, that is, for introduction between the upper and lower incisors of the patient (see FIG. 4). Article 10 further has a rear portion 10B with a longitudinal dimension L2 and having the form of a handle for manipulation by the dentist. The underside 11 of front portion 10A is concave in the form of a circular arc having a radius R; its top side 12 is likewise in the form of a circular arc, possibly with a somewhat larger radius, so that the thickness of front portion 10A, beginning at its leading, or distal, end, increases continuously up to a zone of transition to handle part 10B. Handle part 10B has a lower edge 11' which preferably does not protrude radially inwardly past arc of radius R.

In the exemplary embodiment shown, front portion 10A has a rhomboid cross section, as shown in FIGS. 2b and 2c, in which the length of both the vertical primary axis A and the horizontal primary axis B decrease toward the leading end of front portion 10A.

Markings in the form of shallow grooves or notches 15A ... 15H are provided in top side 12 of front portion 10A and the incisor separation in centric relation position can be read off directly as a result. In the exemplary embodiment shown, four relatively long and deep notches 15A, 15C, 15E and 15G are provided, each indicating a vertical thickness of the shaped article and hence an incisor separation of 4, 3, 2 or 1 mm, respectively, and four shorter and shallower notches 15B, 15D, 15F, 15H are interposed between successive long notches to indicate corresponding intermediate markings representing 0.5 mm increments. A wider groove or notch 15X can receive the central incisor teeth as an aid in making dentures.

Based on the portion of the thus-embodied measurement scale covered or left uncovered by the upper incisors, the dentist can quickly determine the incisor separation in a centric relation location accurately, with a precision as fine as fractions of a millimeter.

In the exemplary embodiment shown, the thickness (vertical primary axis A) of the front portion of the shaped article varies from 0 to 4 mm, and the radius R is 85 mm; it has been found that with this version of the device measurements can be performed for many patients; that is, for many patients, separation of the molars begins with an incisor separation of up to 4 mm. In addition to this, a version can be used in which the thickness (vertical primary axis A) of the front portion 10A extends from 0 to 9 mm, at a radius R of 103 mm. With this version, even greater separations are attainable, with only slightly reduced accuracy.

In the front portion 10B, the handle portion, a bore 13 is provided to retain an adjusting rod 14. The orientation assumed by adjusting rod 14 serves to indicate the horizontal course of the article relative to the occlusion plane and the centric jaw position. Rod 14 also serves the important purpose of preventing aspiration of the article by the patient. Rod 14 may have a length of the order of 90 mm.

The use of the device according to the invention proceeds as follows, reference being made particularly to FIG. 4: First, the patient inclines his head approximately 45° rearward. In this position, both joints of the mandible are positioned by the jaw and neck muscles in their central and most superior places in the glenoid fossae. The teeth are put out of contact for approximately 30 to 60 seconds. This prevents the nerves around the teeth from signalling the brain to establish a different, and undesirable, jaw positioning. The device according to the invention is then introduced between the upper and lower incisors 21) in the vicinity of the 3 or 4 mm marking on its top, with an angle of inclination of approximately 40° to 60°, so that the top 12 of front portion 10A rests on the inside of the upper incisor, or incisors.

If any of the molars or premolars are still in contact with one another at this incisor separation, then the second version of the device should be used (the one having up to 9 mm spacing). The patient now comes into contact slowly, with his mandibular incisors, with the underside of the inclined device. If the patient now bites down lightly on the device with his incisors, there should be no further contact in the vicinity of the premolars and molars. If the premolars and molars are then out of contact, then the distance between the front incisors can be reduced slowly, by slowly pulling out the device, so that the distance between the incisors decreases enough that the premolars and molars are separated only slightly. After any slight corrections that may be necessary in one of two directions, premature contacts or dysfunctions can be checked with foils or other known means. The position of the upper incisors on the scale on the front portion 10A, with both jaw joints correctly positioned, is the desired outcome of measurement as the joint position, which is then recorded for later further diagnostic and therapeutic purposes and can be reproduced at any time as the neuromuscular, and not the tooth-determined, position of the joints.

The transverse groove 15X provided on top side 12 between handle 10B and notch 15A can be used to accommodate the upper central incisors of a complete denture for purposes of recording the centric relation position with greater accuracy than known methods. The thin end of gauge 10 can slide into a small plastic cylinder device secured to the posterior palate of any denture. In this way, the gauge according to the invention would secure, and not dislodge, an upper denture when lower teeth press firmly against underside 11. Incisal biting forces against the device would be transferred to the posterior portion of an upper denture so it would remain firmly against the roof of the mouth while the gauge guides the lower jaw into position.

This application relates to subject matter disclosed in Federal Republic of Germany Application P 38 40 350.1-35, filed on Nov. 30, 1988, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A device for separating the maxillary and mandibular premolars and molars of a dental patient while simultaneously fixing the two jaw joints in centric relation by supporting the maxillary and mandibular incisors by introducing the device between the maxillary and mandibular incisors, said device comprising a front member having a longitudinal dimension and a front end via which said front member is introduced between the maxillary and mandibular incisors, and said front member having a thickness dimension extending between the maxillary and mandibular incisors when said front member is introduced therebetween, said front member being curved in a plane containing the longitudinal and thickness dimensions and the thickness of said front member decreasing toward said front end, wherein said front member has an upper surface which extends along the longitudinal dimension and is located to contact the maxillary incisors when said front member is introduced between the maxillary and mandibular incisors, and said upper surface is provided with markings at uniform intervals along the longitudinal dimension indicating the thickness of said front member in the direction of the thickness dimension.

2. The device of claim 1 made of a nonbrittle sterilizable or autoclavable plastic.

3. The device of claim 1 wherein said front member has a lower surface which extends along the longitudinal dimension and is located to contact the mandibular incisors when said front member is introduced between the maxillary and mandibular incisors, and said front member is curved such that said lower surface is concave and lies on a circular arc.

4. The device of claim 3 further comprising a rear member constituting a handle secured to said front member and configured to not protrude radially inwardly beyond said circular arc.

5. The device of claim 4 wherein said rear member has a horizontal bore for receiving an adjusting rod.

6. The device of claim 3 wherein the radius of the circular arc is between 70 and 120 mm.

7. The device of claim 6 wherein the radius is 85 mm.

8. The device of claim 6 wherein the radius is 103 mm.

9. The device of claim 1 wherein said front member has a transverse cross section having a vertical primary axis parallel to the thickness dimension and a horizontal primary axis perpendicular to said vertical primary axis.

10. The device of claim 9 wherein the length of said vertical primary axis decreases in the direction of the longitudinal dimension toward said front end continuously from a maximum value of 4 mm.

11. The device of claim 12 wherein said front member has a lower surface which extends along the longitudinal dimension and is located to contact the mandibular incisors when said front member is introduced between said maxillary and mandibular incisors, and the said front member being curved such that said lower surface is concave and lies on a circular arc having a radius of 85 mm.

12. The device of claims 9 wherein the length of said vertical primary axis decreases in the direction of the longitudinal dimension toward said front end continuously from a maximum value 9 mm.

13. The device of claim 12 wherein said front member has a lower surface which extends along the longitudinal dimension and is located to contact the mandibular incisors when said front member is introduced between the maxillary and mandibular incisors, and said front member being curved such that said lower surface is concave and lies on a circular arc having a radius of 103 mm.

14. The device of claim 9 wherein the length of said vertical primary axis and the length of said horizontal primary axis decreases in the direction of the longitudinal dimension toward said front end of said front member.

15. The device of claim 1 wherein the linear extent of said front member in the direction of the longitudinal dimension is 45 to 50 mm.

16. The device of claim 1 wherein said markings include grooves or notches.

17. The device of claim 1 wherein said markings indicate the thickness of said front member at intervals each of 0.5 mm.

18. A device for separating the maxillary and mandibular premolars and molars of a dental patient while simultaneously fixing the two jaw joints in centric relation by supporting the maxillary and mandibular incisors by introducing the device between the maxillary and mandibular incisors, said device comprising a front member having a longitudinal dimension and a front end via which said front member is introduced between the maxillary and mandibular incisors, and said front member having a thickness dimension extending between the maxillary and mandibular incisors when said front member is introduced therebetween, said front member being curved in a plane containing the longitudinal and thickness dimensions and the thickness of said front member decreasing toward said front end wherein said front member has a transverse cross section having a vertical primary axis parallel to the thickness dimension and a horizontal primary axis perpendicular to said vertical primary axis and the transverse cross section is at least approximately elliptical.

19. A device for separating the maxillary and mandibular premolars and molars of a dental patient while simultaneously fixing the two jaw joints in centric relation by supporting the maxillary and mandibular incisors by introducing the device between the maxillary and mandibular incisors, said device comprising a front member having a longitudinal dimension and a front end via which said front member is introduced between the maxillary and mandibular incisors, and said front member having a thickness dimension extending between the maxillary and mandibular incisors when said front member is introduced therebetween, said front member being curved in a plane containing the longitudinal and thickness dimensions and the thickness of said front member decreasing toward said front end wherein said front member has a transverse cross section having a vertical primary axis parallel to the thickness dimension and a horizontal primary axis perpendicular to said vertical primary axis and the transverse cross section is rhomboid with rounded corners.

20. A device for separating the maxillary and mandibular premolars and molars o a dental patient while simultaneously fixing the two jaw joints in centric relation by supporting the maxillary and mandibular incisors by introducing the device between the maxillary and mandibular incisors, said device comprising a front member having a longitudinal dimension and a front end via which said front member is introduced between the maxillary and mandibular incisors, and said front member having a thickness dimension extending between the maxillary and mandibular incisors when said front member is introduced therebetween, said front member being curved in a plane containing the longitudinal and thickness dimensions and the thickness of said front member decreasing toward said front end wherein said front member is provided with a transverse groove at the end thereof remote from said front end for engagement by the upper central incisors of a denture.

21. A device for separating the maxillary and mandibular premolars and molars of a dental patient while simultaneously fixing the two jaw joints in centric relation by supporting the maxillary and mandibular incisors by introducing the device between the maxillary and mandibular incisors, said device comprising a front member having a longitudinal dimension and a front end via which said front member is introduced between the maxillary and mandibular incisors, and said front member having a thickness dimension extending between the maxillary and mandibular incisors when said front member is introduced therebetween, said front member being curved in a plane containing the longitudinal and thickness dimensions and the thickness of said front member decreasing toward said front end wherein said front member is provided with a transverse groove at the end thereof remote from said front end for engagement by the upper central incisors of a denture, said device being arranged to have a plastic cylinder mounted at said front end and attached to a posterior palate of an upper denture for improving denture jaw registration by maintaining upper denture placement as lower incisors or facsimile exert force on said front member anteriorly.

* * * * *